United States Patent
Dupuis (12)

(10) Patent No.: US 6,630,133 B1
(45) Date of Patent: *Oct. 7, 2003

(54) COSMETIC COMPOSITION COMPRISING AT LEAST ONE SILICONE/ACRYLATE COPOLYMER AND AT LEAST ONE THICKENING AGENT

(75) Inventor: Christine Dupuis, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/662,804

(22) Filed: Sep. 15, 2000

(30) Foreign Application Priority Data

Sep. 16, 1999 (FR) .............................................. 99 11598

(51) Int. Cl.$^7$ .............................. A61K 7/06; A61K 7/00
(52) U.S. Cl. ................. 424/70.1; 424/70.11; 424/70.12; 424/70.16; 424/401
(58) Field of Search ................................ 424/401, 70.1, 424/70.11, 70.12, 70.14, 70.122, 70.121, 70.16, 70.15, 70.17

(56) References Cited

U.S. PATENT DOCUMENTS

| | | | |
|---|---|---|---|
| 2,798,053 A | | 7/1957 | Brown |
| 2,923,692 A | | 2/1960 | Ackerman et al. |
| 4,237,243 A | | 12/1980 | Quack et al. |
| 6,056,945 A | * | 5/2000 | Cauwet-Martin et al. .. 424/70.1 |
| 6,093,410 A | * | 7/2000 | Peffly et al. ................. 424/401 |

FOREIGN PATENT DOCUMENTS

| | | |
|---|---|---|
| EP | 0 408 311 | 1/1991 |
| FR | 2 416 723 | 9/1979 |
| WO | WO 99/04750 | 2/1999 |
| WO | WO 01/13884 A2 | 3/2001 |

OTHER PUBLICATIONS

Co–pending Application No. 09/662,805; Attorney Docket No. 05725.0751–00000 Title: Cosmetic Composition Comprising at Least One Silicone/Acrylate Copolymer and at Least One Photoprotective Agent Inventor(s): Christine Dupuis U.S. Filing Date: Sep. 15, 2000.

Co–pending Application No. 09/664,402; Attorney Docket No. 05725.0752–00000 Title: Cosmetic Composition Comprising at Least One Silicone/Acrylate Copolymer and at Least One Conditioning Agent Inventor(s): Christine Dupuis U.S. Filing Date: Sep. 18, 2000.

Co–pending Application No. 09/663,183; Attorney Docket No. 05725.0753–00000 Title: Cosmetic Composition Comprising at Least One Silicone/Acrylate Copolymer and at Least One Nonionic Polymer Comprising at Least One Vinyllactam Unit Inventor(s): Christine Dupuis U.S. Filing Date: Sep. 15, 2000.

Co–pending Application No. 09/663,168; Attorney Docket No. 05725.0754–00000 Title: Cosmetic Composition Comprising at Least One Silicone/Acrylate Copolymer and at Least One Grafted Silicone Polymer Inventor(s): Christine Dupuis U.S. Filing Date: Sep. 15, 2000.

Co–pending Application No. 09/662,796; Attorney Docket No. 05725.0755–00000 Title: Aerosol Device Comprising a Hair Composition Comprising at Least one Silicone/Acrylate Copolymer Inventor(s): Christine Dupuis U.S. Filing Date: Sep. 15, 2000.

Translation of WO 99/04750, published Feb. 4, 1999.

* cited by examiner

Primary Examiner—Thurman K. Page
Assistant Examiner—Blessing Fubara
(74) Attorney, Agent, or Firm—Finnegan, Henderson, Farabow, Garrett & Dunner, LLP

(57) ABSTRACT

A cosmetic composition comprising at least one silicone/acrylate copolymer and at least one non-cellulose thickening agent, wherein the at least one silicone/acrylate copolymer is obtained by radical-mediated polymerization of at least one ethylenically unsaturated monomer (a) in the presence of at least one silicone derivative (b) comprising at least one oxyalkylene group. A cosmetic process, in particular a process for fixing and/or holding the hairstyle by using said composition, as well as to the use of this composition for the manufacture of a cosmetic formulation intended in particular for holding and/or shaping the hairstyle.

59 Claims, No Drawings

COSMETIC COMPOSITION COMPRISING AT LEAST ONE SILICONE/ACRYLATE COPOLYMER AND AT LEAST ONE THICKENING AGENT

The invention relates to cosmetic compositions comprising at least one specific silicone/acrylate copolymer and at least one thickening agent. The invention also relates to cosmetic processes, in particular processes for fixing and/or holding the hairstyle by using said compositions, as well as to processes for manufacturing cosmetic formulations comprising including in said formulations at least one composition according to the invention.

Thickened compositions, in particular hair gels, which are generally applied to the hair before placing the hair in shape, are known. A blow-drying or hairsetting operation is then carried out to shape the hair and set the hairstyle. These thickened compositions, in particular these gels, can contain polymeric resins.

However, they can have the drawback of adversely affecting the cosmetic properties of the hair. Thus, the hair may become coarse and difficult to disentangle, it may lose its pleasant feel and appearance or it may lack body. Such cosmetic hair compositions which afford improved cosmetic properties, in particular in terms of at least one of disentangling, softness and feel, are thus sought.

In addition, thickened cosmetic hair compositions can also have the drawback of giving rise to a powdering effect. For the purposes of the present invention, the term "powdering" means the aptitude of the material obtained, on drying of the hair composition, to form a powder after it has been applied to the hair. Accordingly, some unpleasant effects can be that the powder can fall on the user's shoulders or clothing, or attach to the comb or brush.

Thus, it would be advantageous to find thickened cosmetic hair compositions, in particular gels, which overcome at least one of the drawbacks indicated above, and which in particular fix the hairstyle well, while at the same exhibit good cosmetic properties, and which do so without a powdering effect.

The inventor has discovered, surprisingly and unexpectedly, that when silicone/acrylate copolymers are combined with thickening agents, it is possible to obtain such a cosmetic composition.

One subject of the invention is a cosmetic composition comprising, in a cosmetically acceptable medium, at least one silicone/acrylate copolymer and at least one non-cellulose thickening agent, wherein the at least one silicone/acrylate copolymer can be obtained by radical-mediated polymerization of at least one ethylenically unsaturated monomer (a) in the presence of at least one silicone derivative (b) comprising at least one oxyalkylene group.

Another subject of the invention relates to a cosmetic hair process, in particular a process for fixing and/or holding the hairstyle using said composition.

Yet another subject of the invention relates to the use of this composition for the manufacture of a cosmetic hair formulation which is intended in particular for holding and/or shaping the hairstyle.

Representative silicone/acrylate copolymers targeted by the present invention include those described in International patent application WO 99/04750. Specifically, the copolymer sold by BASF under the name Luviflex Silk can be used. This polymer is a grafted copolymer of tert-butyl acrylate/methacrylic acid and silicone copolyol.

For example, the at least one ethylenically unsaturated monomer (a) can be chosen from at least one monomer of formula ($I_a$):

$$X\text{---}\underset{\underset{O}{\|}}{C}\text{---}CR^7\text{=}CHR^6 \quad (I_a)$$

in which:
X is chosen from OH, OM, OR$^8$, NH$_2$, NHR$^8$ and N(R$^8$)$_2$ wherein:
R$^8$, which may be identical or different, are each chosen from hydrogen atoms, linear and branched C$_1$ to C$_{40}$ alkyl groups, optionally substituted with at least one group chosen from alkoxy groups, amino groups and carboxyl groups, monohydroxylated linear and branched C$_1$ to C$_{40}$ alkyl groups, optionally substituted with at least one group chosen from alkoxy groups, amino groups and carboxyl groups, polyhydroxylated linear and branched C$_1$ to C$_{40}$ alkyl groups, optionally substituted with at least one group chosen from alkoxy groups, amino groups and carboxyl groups, hydroxylated polyethers; and
M is chosen from Na$^+$, K$^+$, Mg$^{++}$, NH$^{4+}$, an alkylammonium group, a dialkylammonium group, a trialkylammonium group and a tetraalkylammonium group; and
R$^7$ and R$^6$, which may be identical or different, are each chosen from hydrogen atoms, linear and branched C$_1$ to C$_8$ alkyl groups, methoxy groups, ethoxy groups, 2-hydroxyethoxy groups, 2-methoxyethoxy groups, 2-ethoxyethyl groups, CN groups, COOH groups and COOM groups, wherein M is defined as above.

For example R$^8$, which may be identical or different, can each be chosen from N,N-dimethylaminoethyl groups, 2-hydroxyethyl groups, 2-methoxyethyl groups, 2-ethoxyethyl groups, hydroxypropyl groups, methoxypropyl groups and ethoxypropyl groups.

In the present invention, the at least one monomer of formula ($I_a$) can be chosen from acrylic acid and its salts, esters and amides. The at least one monomer of formula ($I_a$) may also optionally be substituted. For example, the at least one monomer of formula ($I_a$) can also be chosen from methacrylic acid, ethacrylic acid and 3-cyanoacrylic acid.

The at least one monomer of formula ($I_a$) can also be chosen from esters which may be chosen from derivatives of linear C$_1$ to C$_{40}$ alkyls, derivatives of branched C$_3$ to C$_{40}$ alkyls, derivatives of C$_3$ to C$_{40}$ carboxylic alcohols, derivatives of polyfunctional alcohols comprising 2 to 8 hydroxyl groups, derivatives of alcohol ethers and derivatives of polyalkylene glycols. Non-limiting examples of polyfunctional alcohols comprising 2 to 8 hydroxyl groups which may be used according to the present invention include ethylene glycol, hexylene glycol, glycerol and 1,2,6-hexanetriol. Non-limiting examples of alcohol ethers which may be used according to the present invention include methoxymethanol and ethoxyethanol.

The at least one monomer of formula ($I_a$) can also be chosen from N,N-dialkylaminoalkyl acrylates, N,N-dialkylaminoalkyl methacrylates, N-dialkylaminoalkyl acrylamides and N-dialkylaminoalkyl methacrylamides, wherein the amide group may optionally be unsubstituted, N-alkyl-monosubstituted, N-alkylamino-monosubstituted or N,N-dialkylamino-disubstituted, and wherein the alkyl and alkylamino groups are chosen from groups derived from linear C$_1$ to C$_{40}$ carboxylic units and groups derived from branched C$_3$ to C$_{40}$ carboxylic units.

The at least one ethylenically unsaturated monomer (a) can be chosen from $C_1$ to $C_{40}$ vinyl esters, $C_1$ to $C_{40}$ allyl esters, linear $C_3$ to $C_{40}$ carboxylic acids, branched $C_3$ to $C_{40}$ carboxylic acids, vinyl halides, allyl halides, vinyllactams, heterocyclic compounds substituted with at least one group chosen from vinyl groups and allyl groups, N-vinylimidazoles, diallylamines, vinylidene chloride, carbon-based unsaturated compounds, acrylic acid derivatives quaternized with epichlorohydrin and methacrylic acid derivatives quaternized with epichlorohydrin. Non-limiting examples of vinyllactams include vinylpyrrolidone and vinylcaprolactam. Non-limiting examples of heterocyclic compounds substituted with at least one group chosen from vinyl groups and allyl groups include vinylpyridine, vinyloxazoline and allylpyridine. Non-limiting examples of carbon-based unsaturated compounds include styrene and isoprene.

In one embodiment, the at least one ethylenically unsaturated monomer (a) is chosen from N-vinylimidazoles, diallylamines, vinylidene chloride, carbon-based unsaturated compounds, acrylic acid derivatives quaternized with epichlorohydrin and methacrylic acid derivatives quaternized with epichlorohydrin.

Representative at least one ethylenically unsaturated monomers (a) according to the present invention comprise acrylic acid, methacrylic acid, ethacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, propyl ethacrylate, n-butyl ethacrylate, isobutyl ethacrylate, t-butyl ethacrylate, 2-ethylhexyl ethacrylate, decyl ethacrylate, 2,3-hydroxypropyl acrylate, 2,3-dihydroxypropyl methacrylate, 2-dihydroxyethyl acrylate, hydroxypropyl acrylate, 2-hydroxyethyl methacrylate, 2-hydroxyethyl ethacrylate, 2-methoxyethyl acrylate, 2-ethoxyethyl methacrylate, 2-ethoxyethyl ethacrylate, hydroxypropyl methacrylate, glyceryl monoacrylate, glyceryl monomethacrylate, polyalkylene glycol (meth) acrylates, unsaturated sulphonic acids, acrylamide, methacrylamide, ethacrylamide, N,N-dimethylacrylamide, N-ethylacrylamide, N-ethylmethacrylamide, 1-vinylimidazole, N,N-dimethylaminoethyl (meth)acrylate, maleic acid, fumaric acid, maleic anhydride, monoesters of maleic anhydride, crotonic acid, itaconic acid, vinyl ethers, vinylformamide, vinylamine, vinylpyridine, vinylimidazole, vinylfuran, styrene, styryl sulphonate and allyl alcohol.

According to the present invention, the at least one ethylenically unsaturated monomer (a) can also comprise at least one entity chosen from silicon atoms, fluorine atoms and thio groups.

If the at least one ethylenically unsaturated monomer (a) comprises at least one acid group, the at least one acid group can be neutralized before or after polymerization, and partially or totally, such that the solubility and/or the degree of dispersion in water is adjusted to the desired level. Non-limiting examples of agents which may be used for the neutralization according to the present invention include mineral bases and organic bases. For example, the mineral base can be chosen from sodium carbonate. Representative organic bases are amino alcohols and diamines. For example, amino alcohols can be chosen from alkanolamines and these alkanolamines can be chosen from methanolamine, 2-amino-2-methyl-1-propanol and triethanolamine. A representative diamine is lysine.

Further, if the at least one ethylenically unsaturated monomer (a) comprises at least one basic nitrogen atom, the at least one basic nitrogen atom can be quaternized. Similarly, if the at least one ethylenically unsaturated monomer (a) comprises at least two ethylenic double bonds, the at least one ethylenically unsaturated monomer (a) can be at least partially crosslinked.

In the present invention, the at least one silicone derivative (b) suitable for use in the present invention can be chosen from compounds known under the INCI names as dimethicone copolyols and silicone surfactants. For example, the compounds sold under the brand names Abil® by Goldschmidt, Alkasil® by Rhône-Poulenc, silicone Polyol Copolymer® by Genesee, Besil® by Wacker, Silwet® by OSI and Dow Corning 190® by Dow Corning may be used.

In one embodiment, the at least one silicone derivative (b) is chosen from at least one derivative of formula I:

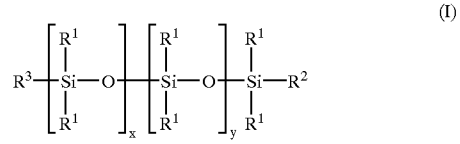

(I)

in which:

x and y, which may be identical or different, are each chosen from integers such that the number molecular weight of said at least on e silicone/acrylate copolymer ranges from 300 to 30,000;

$R^2$ and $R^3$, which may be identical or different, are each chosen from $CH_3$ and groups of formula:

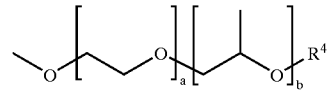

in which:

$R^4$ is chosen from hydrogen, $CH_3$, groups of formula:

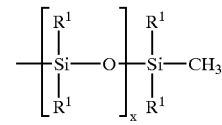

in which:

x is an integer chosen such that the number average molecular weight of said at least one silicone/ acrylate copolymer ranges from 300 to 30,000; and $R^1$, which may be identical or different, are each chosen from $C_1$ to $C_{20}$ aliphatic hydrocarbons, $C_3$ to $C_{20}$ aromatic groups, $C_3$ to $C_{20}$ cycloaliphatic hydrocarbons, groups comprising both aromatic groups and aliphatic groups and groups of formula:

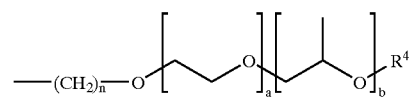

in which:

n is an integer ranging from 1 to 6;

a and b, which may be identical or different, are each chosen from integers ranging from 0 to 50; and and $R^4$ is defined as above;

and groups of formula:

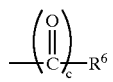

in which:

c is equal to 0 or 1; and $R^6$ is chosen from a $C_1$ to $C_{40}$ group, optionally comprising at least one group chosen from amino groups, carboxyl groups and sulfonyl groups, and, if c is equal to zero, $R_6$ is chosen from an anion of an inorganic acid; and $R^1$, which may be identical or different, are each chosen from $C_1$ to $C_{20}$ aliphatic hydrocarbons, $C_3$ to $C_{20}$ aromatic groups, $C_3$ to $C_{20}$ cycloaliphatic hydrocarbons, groups comprising both aromatic groups and aliphatic groups, and groups of formula:

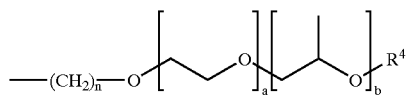

in which:

n is an integer ranging from 1 to 6;

a and b, which may be identical or different, are each chosen from integers ranging from 0 to 50; and $R^4$ is defined as above;

with the proviso that said at least one silicone derivative (b) comprises at least one oxyalkylene group.

In the present invention, $R^1$, which may be identical or different, can be chosen from methyl groups, ethyl groups, propyl groups, butyl groups, isobutyl groups, pentyl groups, isopentyl groups, hexyl groups, octyl groups, decyl groups, dodecyl groups, octadecyl groups, cycloaliphatic groups, aromatic groups and groups comprising both aromatic and aliphatic groups. For example, cycloaliphatic groups can be chosen from cyclohexyl groups. Representative aromatic groups comprise phenyl groups and naphthyl groups. Representative groups comprising both aromatic and aliphatic groups comprise benzyl groups, phenylethyl groups, tolyl groups and xylyl groups.

In the present invention, $R^4$ can be chosen from groups of formula —$(CO)_c$—$R^6$, wherein when c is equal to 1, $R^6$ can be chosen from a group comprising from 1 to 40 carbon atoms, optionally additionally comprising at least one group chosen from $NH_2$ groups, COOH groups and $SO_3H$ groups, wherein said group comprising 1 to 40 carbon atoms can be chosen from an alkyl group, a cycloalkyl group and an aryl group. In one embodiment, $R^4$ is chosen from groups of formula —$(CO)_c$—$R^6$, wherein c is equal to zero and $R^6$ is chosen from phosphates and sulphates.

For example, the at least one silicone derivative (b) can be chosen from at least one derivative of formula:

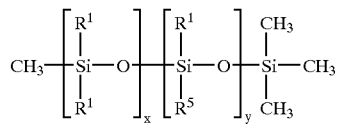

wherein $R_1$, x and y are as previously described and $R^5$, which may be identical or different, can each be chosen from groups of formula:

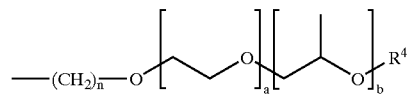

in which n can be an integer ranging from 1 to 6, a and b, which may be identical or different, can each be chosen from integers ranging from 0 to 50 and $R^4$ is as defined above, with the proviso that said at least one silicone derivative (b) comprises at least one oxyalkylene unit.

According to the present invention, the at least one silicone derivative (b) may be present in a proportion generally ranging from 0.1% to 50% by weight relative to the total weight of the at least one silicone/acrylate copolymer. For example, the at least one silicone derivative (b) may be present in a proportion ranging from 1% to 20% by weight relative to the total weight of the at least one silicone/acrylate copolymer.

The at least one silicone/acrylate copolymer can be chosen from, for example, water-soluble silicone/acrylate copolymers and silicone/acrylate copolymers having a dispersibility in water is such that, in a water/ethanol mixture dosed at 50/50 by volume, they are soluble in a proportion of generally greater than 0.1 g/l, such as greater than 0.2 g/l.

The composition of the present invention can generally comprise from 0.1% to 20% of the at least one silicone/acrylate copolymer relative to the total weight of the composition, such as from 0.5% to 10%.

The composition of the present invention can generally comprise from 0.05% to 10% of the at least one non-cellulose thickening agent relative to the total weight of the composition, such as from 0.1% to 5%.

The composition can also comprise at least one silicone derivative chosen from dimethicone copolyols and silicone surfactants.

For the purposes of the present invention, the expression "non-cellulose thickening agent" means a thickening agent whose chemical formula is free of cellulose groups. As natural thickening agents which are suitable for the invention, mention may be made of xanthan gum, scieroglucan gum, gellan gum, rhamsan gum, alginates, maltodextrin, starch and derivatives thereof, karaya gum, carob flour and guar gums.

The synthetic thickening agents according to the invention can include acrylic and/or methacrylic acid polymers or copolymers, such as acrylic acid/ethyl acrylate copolymers and carboxyvinyl polymers. Examples of such polymers or copolymers are, in particular, the "carbomer" (CTFA) products sold by the company Goodrich under the name Carbopol, or polyglyceryl methacrylate sold by the company Guardian under the name Lubragel, or alternatively the polyglyceryl acrylate sold under the name Hispagel by the company Hispano Chimica.

Other acrylic compounds which may be mentioned are acrylic or methacrylic acid copolymers comprising at least one $C_1$ to $C_{30}$ alkyl acrylate unit and/or a urethane unit optionally substituted with a fatty chain. Mention may be made in particular of Pemulen TR1 (Goodrich), Viscophobe DB 1000 (Union Carbide) and Acrysol 44 or 46 (Rohm & Haas).

Thickening agents which may also be used are polyethylene glycols (PEG) and derivatives thereof.

Thickening polyacrylamides can also be used as thickening agents. Representative examples include:
- crosslinked 2-acrylamido-2-methyl-propanesulphonic homopolymers, optionally crosslinked copolymers of acrylamide and of ammonium acrylate,
- optionally crosslinked copolymers of acrylamide (or of methacrylamide) and of methacryloyloxyethyltrimethylammonium chloride,
- optionally crosslinked, partially or totally neutralized copolymers of acrylamide and of 2-acrylamido-2-methylpropanesulphonic acid.

As acrylamide/ammonium acrylate crosslinked copolymers, used in accordance with the present invention, mention may be made more particularly of acrylamide/ammonium acrylate copolymers (5/95 by weight) crosslinked with a crosslinking agent containing polyolefinic unsaturation, such as divinylbenzene, tetraallyloxyethane, methylenebisacrylamide, diallyl ether, polyallylpolyglyceryl ethers or allylic alcohol ethers of the sugar series, such as erythritol, pentaerythritol, arabitol, mannitol, sorbitol or glucose.

Similar copolymers are described and prepared in French patent FR-2 416 723 and U.S. Pat. Nos. 2,798,053 and 2,923,692, the disclosures of which are incorporated by reference herein.

In one embodiment of the invention, this type of crosslinked copolymer can be used in particular in the form of a water-in-oil emulsion comprising about 30% by weight of said copolymer, 25% by weight of liquid paraffin, 4% by weight of a mixture of sorbitan stearate and of a hydrophilic ethoxylated derivative, and 41% by weight of water. Such an emulsion is sold under the name "Bozepol C" by the company Hoechst.

The copolymers of acrylamide and of 2-acryl-amido-2-methylpropanesulphonic acid, which can be used in accordance with the present invention, include copolymers crosslinked with a compound containing polyolefinic unsaturation, such as those mentioned above, and partially or totally neutralized with a neutralizing agent such as sodium hydroxide, potassium hydroxide, aqueous ammonia or an amine such as triethanolamine or monoethanolamine.

They can be prepared by copolymerizing acrylamide and sodium 2-acrylamido-2-methyl-propanesulphonate via a radical route by means of initiators such as azobisisobutyronitrile and by precipitation in an alcohol such as tert-butanol.

Additionally, the copolymers can be obtained by copolymerization of 70 mol % to 55 mol % of acrylamide and of 30 mol % to 45 mol % of sodium 2-acrylamido-2-methylpropanesulphonate, wherein the crosslinking agent can be used at concentrations generally ranging from $1 \times 10^{-4}$ mol to $4 \times 10^{-4}$ mol per mole of the mixture of monomers.

These specific copolymers can be incorporated into the compositions of the invention in the form of water-in-oil emulsions containing from 35% to 40% by weight of this copolymer, from 15% to 25% by weight of a mixture of $C_{12}$–$C_{13}$ isoparaffinic hydrocarbons, and from 3% to 8% by weight of polyethylene glycol lauryl ether containing 7 mol of ethylene oxide and water. Such an emulsion is sold under the name "Sepigel 305" by the company SEPPIC.

The crosslinked copolymer of acrylamide and of methacryloyloxyethyltrimethylammonium chloride, which is used according to the invention, can be a copolymer obtained by copolymerization of acrylamide and of dimethylaminoethyl methacrylate quaternized with methyl chloride, followed by crosslinking with a compound containing olefinic unsaturation, in particular methylenebisacrylamide.

An acrylamide/methacryloyloxyethyltrimethylammonium chloride crosslinked copolymer (about 50/50 by weight) in the form of a dispersion containing 50% by weight of said copolymer in mineral oil can be used. This dispersion is sold under the name "Salcare SC92" by the company Allied Colloids.

The non-crosslinked copolymers of methacrylamide and of methacryloyloxyethyltrimethylammonium chloride are, for example, the products sold under the trade names Rohagit KF 400 and KF 720 by the company Rohm & Haas.

In one embodiment of the invention, the polymers in the cosmetic compositions can have, in solution or dispersion, at 1% active material in water, a viscosity, measured using a Rheomat RM 180 rheometer, at 25° C. of greater than 0.1 ps and even more advantageously greater than 0.2 cp, at a shear rate of 200 $s^{-1}$.

The cosmetically acceptable medium can comprise water or one or more cosmetically acceptable solvents such as alcohols or water/solvent(s) mixtures, wherein the solvents can include $C_1$–$C_4$ alcohols.

Generally, among these alcohols which may be mentioned are ethanol and isopropanol. In particular, ethanol can be used.

The composition of the invention can also contain at least one additive chosen from anionic, cationic, nonionic and amphoteric surfactants other than those of the invention, fragrances, screening agents, preserving agents, proteins, vitamins, polymers other than those of the invention, plant, mineral or synthetic oils and any other additive conventionally used in cosmetic compositions.

A person skilled in the art should take care to select the optional compound(s) to be added to the composition according to the invention such that the advantageous properties associated with the composition in accordance with the invention are not, or are not substantially, adversely affected by the addition envisaged.

These compositions may be packaged in various forms, in particular in pump-dispenser bottles or in aerosol containers, in order to ensure application of the composition in vaporized form or in the form of a mousse. Such packaging forms are indicated, for example, when it is desired to obtain a spray, a lacquer or a mousse for fixing or treating hair. The compositions in accordance with the invention can also be in the form of creams, gels, emulsions, lotions or waxes.

When the composition according to the invention is packaged in aerosol form in order to obtain a lacquer or a mousse, it comprises at least one propellant which may be chosen from volatile hydrocarbons, such as n-butane, propane, isobutane and pentane; and halogenated hydrocarbons. Other representative propellants can include carbon dioxide, nitrous oxide, dimethyl ether (DME), nitrogen and compressed air and, in particular, dimethyl ether.

The propellant in the aerosol device is present in a concentration generally ranging from 5% to 90% by weight relative to the total weight of the composition such as at a concentration ranging from 10% to 60%.

The compositions in accordance with the invention can be applied to the skin, the nails, the lips, the hair, the eyebrows and the eyelashes.

The compositions in accordance with the invention are particularly suitable for dry or wet hair, as styling products.

The invention will be illustrated more fully with the aid of the following non-limiting example. As used herein, "A.M." means active material. As used herein, "PDMS" means polydimethyl silicone. As used herein, "AMP" means 2-amino-2-methyl-1-propanol.

All the percentages are relative percentages by weight with respect to the total weight of the composition.

EXAMPLE

The three compositions in accordance with the invention are applied to locks of grams of European natural chestnut-hair.

| Composition 1: | |
| --- | --- |
| Luviflex Silk (1) | 2% a.m. |
| Synthalen (2) | 1% a.m. |
| AMP | qs pH = 8 |
| Ethanol | qs 10% a.m |
| Water | qs 100 g |
| Composition 2: | |
| Luviflex Silk (1) | 2% a.m. |
| Hostacerin AMPS (3) | 2% a.m. |
| AMP | qs pH = 8 |
| Water | qs 100 g |
| Composition 3: | |
| Luviflex Silk (1) | 2% a.m. |
| Viscophobe DB 1000 (4) | 1% a.m. |
| AMP | qs pH =8 |
| Water | qs 100 g |

(1) Silicone/acrylate copolymer sold by BASF (t-butyl acrylate/methacrylic acid/PDMS polyether)
(2) Crosslinked acrylic acid sold by Goodrich,
(3) Crosslinked AMPS sold by Clariant,
(4) Acrylic/urethane terpolymer sold by Union Carbide.

The locks feel soft and look clean, and the compositions give little powdering.

What is claimed is:

1. A cosmetic composition comprising, in a cosmetically acceptable medium, i) at least one silicone/acrylate copolymer comprising at least one oxyalkylene group, and ii) at least one non-cellulose thickening agent, wherein the at least one silicone/acrylate copolymer is obtained by radical-mediated polymerization of at least one ethylenically unsaturated monomer (a) in the presence of at least one silicone derivative (b) comprising at least one oxyalkylene group.

2. A composition according to claim 1, wherein said at least one ethylenically unsaturated monomer (a) is chosen from at least one monomer of formula ($I_a$):

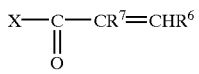

(I$_a$)

in which:
X is chosen from OH, OM, OR$^8$, NH$_2$, NHR$^8$ and N(R$^8$)$_2$, wherein:
R$^8$, which may be identical or different, are each chosen from hydrogen atoms, linear and branched C$_1$ to C$_{40}$ alkyl groups, optionally substituted with at least one group chosen from alkoxy groups, amino groups and carboxyl groups, monohydroxylated linear and branched C$_1$ to C$_{40}$ alkyl groups, optionally substituted with at least one group chosen from alkoxy groups, amino groups and carboxyl groups, polyhydroxylated linear and branched C$_1$ to C$_{40}$ alkyl groups, optionally substituted with at least one group chosen from alkoxy groups, amino groups and carboxyl groups, and hydroxylated polyethers; and
M is chosen from Na$^+$, K$^+$, Mg$^{++}$, NH$^{4+}$, an alkylammonium group, a dialkylammonium group, a trialkylammonium group and a tetraalkylammonium group;
R$^7$ and R$^6$, which may be identical or different, are each chosen from hydrogen atoms, linear and branched C$_1$ to C$_8$ alkyl groups, methoxy groups, ethoxy groups, 2-hydroxyethoxy groups, 2-methoxyethoxy groups, 2-ethoxyethyl groups, CN groups, COOH groups and COOM groups, wherein M is defined as above.

3. A composition according to claim 2, wherein said linear and branched C$_1$ to C$_{40}$ alkyl groups optionally substituted with at least one group chosen from alkoxy groups, amino groups and carboxyl groups are each chosen from N,N-dimethylaminoethyl groups, 2-methoxyethyl groups, 2-ethoxyethyl groups, methoxypropyl groups and ethoxypropyl groups.

4. A composition according to claim 2, wherein said monohydroxylated linear and branched C$_1$ to C$_{40}$ alkyl groups optionally substituted with at least one group chosen from alkoxy groups, amino groups and carboxyl groups are each chosen from 2-hydroxyethyl groups and hydroxypropyl groups.

5. A composition according to claim 2, wherein said at least one monomer of formula ($I_a$) is chosen from acrylic acid, the salts of acrylic acid, esters and amides.

6. A composition according to claim 2, wherein said at least one monomer of formula ($I_a$) is chosen from methacrylic acid, ethacrylic acid and 3-cyanoacrylic acid.

7. A composition according to claim 2, wherein said at least one monomer of formula ($I_a$) chosen from esters is chosen from derivatives of linear C$_1$ to C$_{40}$ alkyls, derivatives of branched C$_3$ to C$_{40}$ alkyls, derivatives of C$_3$ to C$_{40}$ carboxylic alcohols, derivatives of polyfunctional alcohols comprising 2 to 8 hydroxyl groups, derivatives of alcohol ethers and derivatives of polyalkylene glycols.

8. A composition according to claim 7, wherein said polyfunctional alcohols comprising 2 to 8 hydroxyl groups are chosen from ethylene glycol, hexylene glycol, glycerol and 1,2,6-hexanetriol.

9. A composition according to claim 7, wherein said alcohol ethers are chosen from methoxymethanol and ethoxyethanol.

10. A composition according to claim 2, wherein said at least one monomer of formula ($I_a$) is chosen from N,N-dialkylaminoalkyl acrylates, N,N-dialkylaminoalkyl methacrylates, N-dialkylaminoalkyl acrylamides and N-dialkylaminoalkyl methacrylamides, wherein the amide group may optionally be unsubstituted, N-alkyl-monosubstituted, N-alkylamino-monosubstituted or N,N-dialkylamino-disubstituted, and wherein the alkyl moities are chosen from linear C$_1$ to C$_{40}$ alkyl moities and branched C$_3$ to C$_{40}$ alkyl moities.

11. A composition according to claim 1, wherein said at least one ethylenically unsaturated monomer (a) is chosen from C$_1$ to C$_{40}$ vinyl esters, C$_1$ to C$_{40}$ allyl esters, linear C$_3$ to C$_{40}$ carboxylic acids, branched C$_3$ to C$_{40}$ carboxylic acids, vinyl halides, allyl halides, vinyllactams, heterocyclic compounds substituted with at least one group chosen from vinyl groups and allyl groups, N-vinylimidazoles, diallylamines, vinylidene chloride, carbon-based unsaturated compounds, acrylic acid derivatives quaternized with epichlorohydrin and methacrylic acid derivatives quaternized with epichlorohydrin.

12. A composition according to claim 11, wherein said vinyllactams are chosen from vinylpyrrolidone and vinyl-caprolactam.

13. A composition according to claim 11, wherein said heterocyclic compounds substituted with at least one group chosen from vinyl groups and allyl groups are chosen from vinylpyridine, vinyloxazoline and allylpyridine.

14. A composition according to claim 11, wherein said carbon-based unsaturated compounds are chosen from styrene and isoprene.

15. A composition according to claim 1, wherein said at least one ethylenically unsaturated monomer (a) is chosen from N-vinylimidazoles, diallylamines, vinylidene chloride, carbon-based unsaturated compounds, acrylic acid derivatives quaternized with epichlorohydrin and methacrylic acid derivatives quaternized with epichlorohydrin.

16. A composition according to claim 1, wherein said at least one ethylenically unsaturated monomers (a) is chosen from acrylic acid, methacrylic acid, ethacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, propyl ethacrylate, n-butyl ethacrylate, isobutyl ethacrylate, t-butyl ethacrylate, 2-ethylhexyl ethacrylate, decyl ethacrylate, 2,3-hydroxypropyl acrylate, 2,3-dihydroxypropyl methacrylate, 2-dihydroxyethyl acrylate, hydroxypropyl acrylate, 2-hydroxyethyl methacrylate, 2-hydroxyethyl ethacrylate, 2-methoxyethyl acrylate, 2-ethoxyethyl methacrylate, 2-ethoxyethyl ethacrylate, hydroxypropyl methacrylate, glyceryl monoacrylate, glyceryl monomethacrylate, polyalkylene glycol (meth) acrylates, unsaturated sulphonic acids, acrylamide, methacrylamide, ethacrylamide, N,N-dimethylacrylamide, N-ethylacrylamide, N-ethylmethacrylamide, 1-vinylimidazole, N,N-dimethylaminoethyl (meth)acrylate, maleic acid, fumaric acid, maleic anhydride, monoesters of maleic anhydride, crotonic acid, itaconic acid, vinyl ethers, vinylformamide, vinylamine, vinylpyridine, vinylimidazole, vinylfuran, styrene, styryl sulphonate and allyl alcohol.

17. A composition according to claim 1, wherein said at least one ethylenically unsaturated monomer (a) further comprises at least one entity chosen from silicon atoms, fluorine atoms and thio groups.

18. A composition according to claim 1, wherein said at least one silicone derivative (b) is chosen from at least one derivative of formula I:

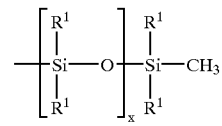

(I)

in which:

x and y, which may be identical or different, are each chosen from integers wherein said integers are chosen such that the number average molecular weight of said at least one silicone/acrylate copolymer ranges from 300 to 30,000;

$R^2$ and $R^3$, which may be identical or different, are each chosen from $CH_3$ and groups of formula:

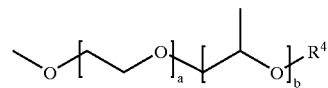

in which:
$R^4$ is chosen from hydrogen, $CH_3$, groups of formula:

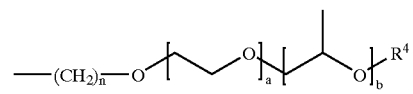

in which:
x is an integer chosen such that the number average molecular weight of said at least one silicone/acrylate copolymer ranges from 300 to 30,000; and
$R^1$, which may be identical or different, are each chosen from $C_1$ to $C_{20}$ aliphatic hydrocarbons, $C_3$ to $C_{20}$ aromatic groups, $C_3$ to $C_{20}$ cycloaliphatic hydrocarbons, groups comprising both aromatic groups and aliphatic groups and groups of formula:

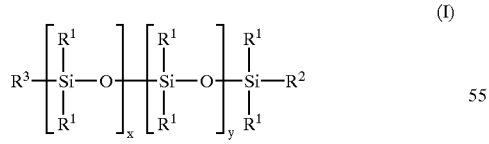

in which:
n is an integer ranging from 1 to 6;
a and b, which may be identical or different, are each chosen from integers ranging from 0 to 50; and
and $R^4$ is defined as above;
and groups of formula:

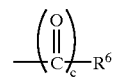

in which:
c is equal to 0 or 1; and
$R^6$ is chosen from a $C_1$ to $C_{40}$ group, optionally comprising at least one group chosen from amino groups, carboxyl groups and sulfonyl groups, and,
if c is equal to zero, $R_6$ is chosen from an anion of an inorganic acid; and
$R^1$, which may be identical or different, are each chosen from $C_1$ to $C_{20}$ aliphatic hydrocarbons, C3 to $C_{20}$ aromatic groups, $C_3$ to $C_{20}$ cycloaliphatic hydrocarbons, groups comprising both aromatic groups and aliphatic groups, and groups of formula:

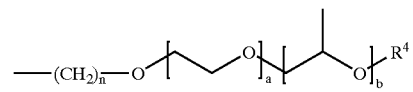

n is an integer ranging from 1 to 6;
a and b, which may be identical or different, are each chosen from integers ranging from 0 to 50; and $R^4$ is defined as above;
with the proviso that said at least one silicone derivative (b) comprises at least one oxyalkylene unit.

19. A composition according to claim 18, wherein said $R^1$, which may be identical or different, are each chosen from methyl groups, ethyl groups, propyl groups, butyl groups, isobutyl groups, pentyl groups, isopentyl groups, hexyl groups, octyl groups, decyl groups, dodecyl groups, octadecyl groups, cycloaliphatic groups, aromatic groups and groups comprising both aromatic and aliphatic groups.

20. A composition according to claim 19, wherein said cycloaliphatic groups are chosen from cyclohexyl groups.

21. A composition according to claim 19, wherein said aromatic groups are chosen from phenyl groups and naphthyl groups.

22. A composition according to claim 19, wherein said groups comprising both aromatic and aliphatic groups are chosen from benzyl groups, phenylethyl groups, tolyl groups and xylyl groups.

23. A composition according to claim 18, wherein said $R^4$ is chosen from groups of formula —$(CO)_c$—$R^6$, wherein c is equal to 1 and $R^6$ is chosen from a group comprising from 1 to 40 carbon atoms, optionally comprising at least one group chosen from $NH_2$ groups, COOH groups and $SO_3H$ groups, wherein said group comprising from 1 to 40 carbon atoms is chosen from an alkyl group, a cycloalkyl group and an aryl group.

24. A composition according to claim 18, wherein said $R^4$ is chosen from groups of formula —$(CO)_c$—$R^6$, wherein c is equal to zero and $R^6$ is chosen from phosphates and sulphates.

25. A composition according to claim 1, wherein said at least one silicone derivative (b) is chosen from at least one derivative of formula:

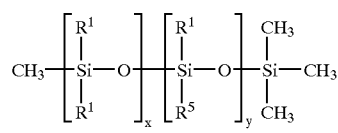

in which:
x and y, which may be identical or different, are each chosen from integers wherein said integers are chosen such that the number average molecular weight of said at least one silicone/acrylate copolymer ranges from 300 to 30,000;

$R^1$, which may be identical or different, are each chosen from $C_1$ to $C_{20}$ aliphatic hydrocarbons, $C_3$ to $C_{20}$ aromatic groups, $C_3$ to $C_{20}$ cycloaliphatic hydrocarbons, groups comprising both aromatic groups and aliphatic groups and groups of formula:

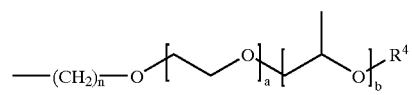

in which:
n is an integer ranging from 1 to 6;
a and b, which may be identical or different, are each chosen from integers ranging from 0 to 50; and
$R^4$ is chosen from hydrogen, $CH_3$, a group of formula:

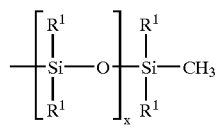

in which:
x is an integer chosen such that the number average molecular weight of said at least one silicone/acrylate copolymer ranges from 300 to 30,000; and $R^1$, which may be identical or different, are each chosen from $C_1$ to $C_{20}$ aliphatic hydrocarbons, $C_3$ to $C_{20}$ aromatic groups, C3 to $C_{20}$ cycloaliphatic hydrocarbons, groups comprising both aromatic groups and aliphatic groups and groups of formula:

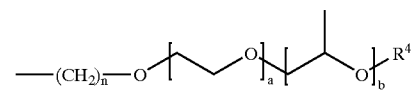

in which:
n is an integer ranging from 1 to 6;
a and b, which may be identical or different, are each chosen from integers ranging from 0 to 50; and
$R^4$ is defined as above; and
a group of formula:

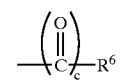

in which:
$R^6$ is chosen from a $C_1$ to $C_{40}$ group, optionally comprising at least one group chosen from amino groups, carboxyl groups and sulfonyl groups, and, if c is equal to zero, $R_6$ is chosen from an anion of an inorganic acid; and
c is equal to 0 or 1; and
$R^5$, which may be identical or different, are each chosen from groups of formula:

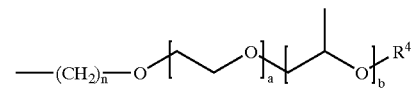

in which:
n is an integer ranging from 1 to 6;
a and b, which may be identical or different, are each chosen from integers ranging from 0 to 50; and
$R^4$ is defined as above;
with the proviso that said at least one silicone derivative (b) comprises at least one oxyalkylene unit.

26. A composition according to claim 1, wherein said at least one silicone derivative (b) is chosen from dimethicone copolyols and silicone surfactants.

27. A composition according to claim 1, wherein said at least one silicone derivative (b) is present in a proportion ranging from 0.1% to 50% by weight relative to the total weight of said at least one silicone/acrylate copolymer.

28. A composition according to claim 27, wherein said at least one silicone derivative (b) is present in a proportion ranging from 1% to 20% by weight relative to the total weight of said at least one silicone/acrylate copolymer.

29. A composition according to claim 1, wherein said at least one silicone/acrylate copolymer is chosen from water-soluble silicone/acrylate copolymers and silicone/acrylate copolymers having a dispersibility in water is such that, in a water/ethanol mixture dosed at 50/50 by volume, said copolymers are soluble in a proportion of greater than 0.1 g/l.

30. A composition according to claim 29, wherein said silicone/acrylate copolymers have a dispersibility in water such that said copolymers are soluble in a proportion of greater than 0.2 g/l.

31. A composition according to claim 1, wherein said at least one silicone/acrylate copolymer is present in a proportion ranging from 0.1% to 20% by weight relative to the total weight of said composition.

32. A composition according to claim 31, wherein said at least one silicone/acrylate copolymer is present in a proportion ranging from 0.5% to 10% by weight relative to the total weight of said composition.

33. The composition according to claim 1, wherein the at least one non-cellulose thickening agent is chosen from thickening agents free of cellulose groups.

34. The composition according to claim 33, wherein the at least one non-cellulose thickening agent is chosen from xanthan gum, scleroglucan gum, gellan gum, rhamsan gum, alginates, maltodextrin, starch and derivatives thereof, karaya gum, carob flour and guar gums; acrylic and methacrylic acid polymers and copolymers; polyethylene glycols and derivatives thereof; polyacrylamides; and copolymers of acrylamide and of acrylamide derivatives.

35. The composition according to claim 33, wherein the acrylic and methacrylic acid polymers and copolymers are chosen from acrylic acid/ethyl acrylate copolymers and carboxyvinyl polymers; and acrylic and methacrylic acid copolymers comprising at least one unit chosen from $C_1$ to $C_{30}$ alkyl acrylate units and urethane units optionally substituted with a fatty chain.

36. The composition according to claim 1, wherein the at least one non-cellulose thickening agent is present in an amount ranging from 0.05% to 10% by weight, relative to the total weight of the composition.

37. The composition according to claim 36, wherein the at least one non-cellulose thickening agent is present in an amount ranging from 0.1% to 5% by weight, relative to the total weight of the composition.

38. The composition according to claim 34, wherein the polyacrylamides are chosen from:
   crosslinked 2-acrylamido-2-methyl-propanesulphonic homopolymers,
   optionally crosslinked copolymers of acrylamide and of ammonium acrylate,
   optionally crosslinked copolymers of acrylamide, of methacrylamide, and of methacryloyloxyethyltrimethylammonium chloride, and
   optionally crosslinked, partially and totally neutralized copolymers of acrylamide and of 2-acrylamido-2-methylpropanesulphonic acid.

39. The composition according to claim 38, wherein the optionally crosslinked copolymers of acrylamide and of ammonium acrylate are chosen from acrylamide/ammonium acrylate copolymers (5/95 by weight) crosslinked with a crosslinking agent comprising polyolefinic unsaturation.

40. The composition according to claim 39, wherein the crosslinking agent comprising polyolefinic unsaturation is chosen from divinylbenzene, tetraallyloxyethane, methylenebisacrylamide, diallyl ether, polyallylpolyglyceryl ethers, and allylic alcohol ethers of the sugar series.

41. The composition according to claim 39, wherein the crosslinking agent comprising polyolefinic unsaturation is chosen from erythritol, pentaerythritol, arabitol, mannitol, sorbitol and glucose.

42. The composition according to claim 39, wherein the acrylamide/ammonium acrylate copolymers (5/95 by weight) crosslinked with a crosslinking agent containing polyolefinic unsaturation comprise a water-in-oil emulsion comprising about 30% by weight of the copolymer, 25% by weight of liquid paraffin, 4% by weight of a mixture of sorbitan stearate and of a hydrophilic ethoxylated derivative, and 41% by weight of water.

43. The composition according to claim 38, wherein the copolymers of acrylamide and of 2-acrylamido-2-methylpropanesulphonic acid are chosen from copolymers crosslinked with a compound containing polyolefinic unsaturation, and partially or totally neutralized with a neutralizing agent chosen from sodium hydroxide, potassium hydroxide, aqueous ammonia, and an amine chosen from triethanolamine and monoethanolamine.

44. The composition according to claim 43, wherein the copolymers of acrylamide and of 2-acrylamido-2-methylpropanesulphonic acid are incorporated into the compositions of the invention in the form of water-in-oil emulsions containing from 35% to 40% by weight of this copolymer, from 15% to 25% by weight of a mixture of $C_{12}$–$C_{13}$ isoparaffinic hydrocarbons, and from 3% to 8% by weight of polyethylene glycol lauryl ether containing 7 mol of ethylene oxide and water.

45. The composition according to claim 38, wherein the crosslinked copolymers of acrylamide and of methacryloyloxyethyltrimethylammonium chloride are chosen from copolymers obtained by copolymerization of acrylamide and of dimethylaminoethyl methacrylate quaternized with methyl chloride; and crosslinked with a compound containing olefinic unsaturation.

46. The composition according to claim 45, wherein the compound containing olefinic unsaturation is methylenebisacrylamide.

47. The composition according to claim 1, wherein the cosmetically acceptable medium is chosen from at least one cosmetically acceptable solvent, and water.

48. The composition according to claim 47, wherein the at least one cosmetically acceptable solvent is chosen from at least one alcohol and mixtures comprising water and at least one solvent.

49. The composition according to claim 48, wherein the at least one solvent is chosen from $C_1$ to $C_4$ alcohols.

50. The composition according to claim 49, wherein the $C_1$ to $C_4$ alcohols are chosen from ethanol and isopropanol.

51. The composition according to claim 50, wherein the $C_1$ to $C_4$ alcohol is ethanol.

52. The composition according to claim 1, further comprising at least one additive chosen from anionic, cationic, nonionic and amphoteric surfactants other than those of the invention, fragrances, preserving agents, proteins, vitamins, polymers other than those of the invention, and plant, mineral and synthetic oils, and any other additive conventionally used in cosmetic compositions.

53. A gel, a spray, a lacquer, a mousse, a cream, an emulsion, a lotion or a wax comprising, in a cosmetically acceptable medium, at least one silicone/acrylate copolymer and at least one non-cellulose thickening agent, wherein the at least one silicone/acrylate copolymer is obtained by radical-mediated polymerization of at least one ethylenically unsaturated monomer (a) in the presence of at least one silicone derivative (b) comprising at least one oxyalkylene group.

54. A gel, a spray, a lacquer, a mousse, a cream, an emulsion, a lotion or a wax according to claim 53, further comprising a styling product suitable for dry or wet hair.

55. A process for fixing, holding or shaping the hairstyle, comprising applying to hair a composition comprising, in a cosmetically acceptable medium, at least one silicone/acrylate copolymer and at least one non-cellulose thickening agent, wherein the at least one silicone/acrylate copolymer is obtained by radical-mediated polymerization of at least one ethylenically unsaturated monomer (a) in the presence of at least one silicone derivative (b) comprising at least one oxyalkylene group.

56. A process for manufacturing a cosmetic product comprising including in said product at least one silicone/acrylate copolymer and at least one non-cellulose thickening agent, wherein the at least one silicone/acrylate copolymer is obtained by radical-mediated polymerization of at least one ethylenically unsaturated monomer (a) in the presence of at least one silicone derivative (b) comprising at least one oxyalkylene group.

57. The process according to claim 56, wherein the at least one cosmetic product is a hair product.

58. The process for treating skin, nails, lips, hair, eyebrows or eyelashes comprising applying thereto, in a cosmetically acceptable medium, at least one silicone/acrylate copolymer and at least one non-cellulose thickening agent, wherein the at least one silicone/acrylate copolymer is obtained by radical-mediated polymerization of at least one ethylenically unsaturated monomer (a) in the presence of at least one silicone derivative (b) comprising at least one oxyalkylene group.

59. A composition for treating comprising skin, nails, lips, hair, eyebrows or eyelashes comprising, in a cosmetically acceptable medium, at least one silicone/acrylate copolymer and at least one non-cellulose thickening agent, wherein the at least one silicone/acrylate copolymer is obtained by radical-mediated polymerization of at least one ethylenically unsaturated monomer (a) in the presence of at least one silicone derivative (b) comprising at least one oxyalkylene group.

* * * * *

UNITED STATES PATENT AND TRADEMARK OFFICE
CERTIFICATE OF CORRECTION

PATENT NO. : 6,630,133 B1
DATED : October 7, 2003
INVENTOR(S) : Christine Dupuis It is certified that error appears in the above-identified patent and that said Letters Patent is hereby corrected as shown below:

Column 10,
Lines 51, 52 and 53, "moities" should read -- moieties --.

Column 11,
Line 13, "quatemized" should read -- quaternized --.
Line 16, "one ethylenically unsaturated monomers" should read -- one ethylenically unsaturated monomer --.

Column 12,
Line 34, before "$R^4$ is defined", delete "and".
Line 50, "C3 to $C_{20}$" should read -- $C_3$ to $C_{20}$ --.

Column 14,
Line 7, "C3 to $C_{20}$" should read -- $C_3$ to $C_{20}$ --.

Signed and Sealed this

Twenty-third Day of December, 2003

JAMES E. ROGAN
*Director of the United States Patent and Trademark Office*